United States Patent [19]

Su

[11] Patent Number: 4,501,834

[45] Date of Patent: Feb. 26, 1985

[54] GELS FORMED FROM ANIONIC AND CATIONIC POLYMERS

[75] Inventor: Dean T. Su, North Brunswick, N.J.

[73] Assignee: Colgate-Palmolive Company, New York, N.Y.

[21] Appl. No.: 564,589

[22] Filed: Dec. 22, 1983

[51] Int. Cl.$^3$ .......................... A61K 7/00; A61K 7/06; B32B 21/04

[52] U.S. Cl. ........................................ 524/28; 424/70; 424/73; 424/78; 424/81; 424/DIG. 2; 514/781; 523/105; 524/523

[58] Field of Search .................. 523/105; 524/28, 523; 424/DIG. 2, 70, 73, 78, 81, 381

[56] References Cited

U.S. PATENT DOCUMENTS

| | | | |
|---|---|---|---|
| 3,242,120 | 3/1966 | Steuber | 524/29 |
| 3,715,428 | 2/1973 | Quasius et al. | 424/DIG. 2 |
| 3,980,091 | 9/1976 | Dasher et al. | 424/DIG. 2 |
| 4,128,631 | 12/1978 | Lundmark et al. | 424/78 |
| 4,273,760 | 6/1981 | Koehler et al. | 424/DIG. 2 |
| 4,349,532 | 9/1982 | Vanlerberghe et al. | 424/81 |
| 4,373,011 | 2/1983 | Yin | 524/28 |

FOREIGN PATENT DOCUMENTS

| | | |
|---|---|---|
| 864433 | 2/1971 | Canada . |
| 978938 | 12/1975 | Canada . |
| 2098226 | 11/1982 | United Kingdom . |

Primary Examiner—Ronald W. Griffin
Attorney, Agent, or Firm—Richard N. Miller; Murray M. Grill; Herbert S. Sylvester

[57] ABSTRACT

The formation of novel water soluble and water insoluble gels by interpolymer reactions of selective anionic polymers with selective cationic polymers in an aqueous medium, with either polymer serving as a cross-linking agent under specific conditions of speed and concentration. The selective cationic polymer is a quaternized ammonium polyelectrolyte selected from the group consisting of poly (diallyldimethylammonium chloride), poly (diallyldimethylammonium chloride-co-acrylamide), and a quaternary ammonium cellulose ether polymer. The anionic polymer is selected from the group consisting of a polysulfonic acid and alginic acid. The formation of the gel structure depends on fast and intensive interaction of the two opposite charges to insure a maximum amount of ion pair formation. The solubility of the gel depends on the formation of intimate or loose ion pairs; which depends on the charge density and structure of the polyelectrolytes. These interpolymer gels exhibit a dramatic increase in viscosity. The water soluble gels produced can be used as foam enhancers and conditioning agents in cosmetic compositions such as shaving gels, shampoos and the like; and in sewage treatment (removal of sebum and traces of organic substances). The water insoluble gels are clear and of extremely high viscoelasticity which can be made into clear films.

11 Claims, No Drawings

GELS FORMED FROM ANIONIC AND CATIONIC POLYMERS

This invention relates to the formation of novel water soluble and water insoluble but swellable gels by the interpolymer reactions of selective anionic with selective cationic polymers in an aqueous medium under specific conditions of speed and at specific dilutions.

DESCRIPTION OF THE PRIOR ART

Polyvalent metal ions such as calcium, aluminum and chromium ions are known to from gels with water soluble polymers containing carboxyl groups as shown in Canadian Pat. No. 978938. However, said polyvalent metal ions form mostly water insoluble gels which adversely affect the safety and performance of a detergent composition containing said water insoluble gels, i.e. the foaming ability of the detergent composition is significantly decreased.

Monovalent cations, such as sodium, potassium, monoethanolamine, etc., also react with poly(2-acrylamido-2-methylpropane sulfonic acid) to form gels useful as lubricants in personal care products as shown in U.S. Pat. No. 4,128,631.

A hydrophilic gel reaction product of a polymeric fatty acid polyamide and a diethanolamide of a fatty acid has been used as a detergent as shown in U.S. Pat. No. 3,654,167. Said polyamide polymer reactant may also be pretreated with other polymeric materials prior to the addition of the diethanolamide, such as acrylamide-acrylic acid copolymer, etc. (column 5 lines 33–50) which results in a gel having novel and unique properties. This is a reaction of two anionic polymers.

Although the above cited prior art references disclose the formation of anionic polymer gels, there is no disclosure of the formation of an interpolymer gel by the reaction of a quaternized cationic polymer with an anionic polymer.

Interpolymer reactions of polycationic and polyanionic materials to form reaction products which are in the form of water insoluble precipitates is disclosed in U.S. Pat. No. 4,299,817. U. K. Patent Application No. 2,098,226A (L'Oreal) discloses skin-treating compositions containing a cationic polymer in combination with a vinyl sulfonic anionic polymer, which react on the hair, and may be added in a single composition or in separate compositions. U.S. Pat. No. 4,240,450 (L'Oreal) also describes the interaction of a cationic polymer with an anionic polymer (column 2 lines 11–17), useful in skin and hair treating compositions. These polymer complexes may be preformed on the cationic polymer and anionic polymer may react (column 43 line 57 to column 44 line 38) on the hair. When preformed, said anionic and cationic polymers are mixed in the presence of surfactants in a solvent medium and may form a precipitate which can be solubilized by the anionic surfactant.

None of the aforecited prior art discloses the formation of a gel reaction product free of precipitates, by the interaction of a cationic polymer and an anionic polymer.

*The Journal of Polymer Science*, Vol. 14 (1976) 767–771, which is hereby incorporated by reference, discloses gel formation through interpolymer interaction of poly (methacrylic acid) and poly (vinylbenzyltrimethylammonium cloride ) under specific solution concentrations. Otherwise, precipitation occurs. It is further noted herein, that the gel structure of the interpolymer complex formed at 30° C. in an aqueous medium is irreversibly altered at elevated temperatures as evidenced by its decreased viscosity. However, no irreversible change during heating is observed in an alcoholic medium; and the concentrations to effect gelation instead of precipitation therein is different from that in an aqueous medium. This article clearly illustrates the specific conditions required to form an interpolymer gel by the interaction of specific anionic and cationic polymers.

SUMMARY OF THE INVENTION

It has now been found that water soluble and water insoluble but swellable interpolymer gels free of precipitates can be prepared through the interpolymer reaction of selective anionic polymers with selective cationic polymers under specific conditions of speed and concentration in an aqueous medium free of extraneous materials such as salt, amphoteric compounds, anionic compounds, cationic compounds and the like, which interfere with the formation of the gel structure. The viscosity of present gels is not irreversilby altered due to heat. The gels of this invention can be used in sewage treatment, in the making of clear films, and as a conditioning and gelling agent in personal care compositions such as shaving gels, shampoos, and the like.

Accordingly, it is a primary object of the present invention to prepare water soluble and water insoluble swellable gels through the interpolymer reactions of selective anionic and selective cationic polymers in an aqueous medium free of interfering ingredients.

Another object of this invention is to provide the formation of the gel structure by the fast and intensive interaction of the two oppositely charged polymers to insure a maximum amount of ion pair formation of said two opposite charges.

Still another object of present invention is to provide novel gels made with selective polyelectrolytes which are capable of reversibly retaining its viscous gel structure upon heating and cooling.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel water soluble and water insoluble swellable interpolymer gels of this invention comprises the reaction product formed by the rapid and intensive interaction of two oppositely charged selective polymers.

The oppositely charged polymers are a quaternized cationic polymer bearing positive charges and an anionic polymer bearing negative charges selected from the group consisting of polysulfonic acid and an alginic acid.

More specifically, the interpolymer gels of this invention are prepared by reacting a cationic polymer selected from the group consisting of poly (diallyldimethylammonium chloride), poly (diallyldimethylammonium chloride-co-acrylamide), and a quaternary ammonium cellulose ether polymer with an anionic polymer selected from the group consisting of poly (2-acrylamido-2-methylpropane sulfonic acid) and alginic acid, in an aqueous medium containing high concentrations of said polymer reactants, with vigorous mixing. Low aqueous concentration of said polymer reactants cause precipitation of the polyion complex. Also, slow mixing produces white precipitates and not gels.

The method of preparing the interpolymer gels of present invention comprises the rapid mixing, at a rate of at least 500 rpm, preferably at least about 1000 rpm, of specified aqueous concentrations of selective anionic and selective cationic polymers in an aqueous medium substantially free of interfering ingredients such as salt, amphoteric, anionic and cationic compounds.

More specifically, aqueous solutions of the cationic polymer are admixed with the aqueous solution of the anionic polymer, or either the anionic polymer or the cationic polymer in powdered form may be added to an aqueous solution of the oppositely charged polymer and vigorously mixed. The order of addition is immaterial, provided the essential conditions of speed and concentration are present and the specific group of polymers are used as reactants in the production of the polyelectrolyte complex in the form of a clear gel, free of precipitates. A hazy gel is indicative of the presence of precipitates. The gels prepared according to present invention are stable, i.e., they retain their gel structure under conditions of heating or cooling and return to their original viscosity at room temperature. After the gel is formed, it can be thinned without losing its gel structure. The interpolymer gel may be thick and viscous and non-pourable or substantially non-pourable.

DETAILED DESCRIPTION OF THE INVENTION

The selective group of quaternized cationic polymers used in present invention are water soluble include:

1. Poly (diallyldimethylammonium chloride) having a molecular weight between 75,000 and 500,000 which contains dimethylallyammonium chloride units of the following formula:

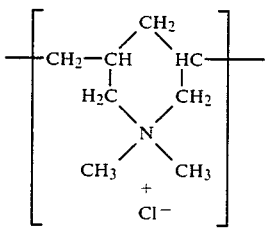

A preferred polymer having a molecular weight less than 100,000 is obtainable as a 40% (by weight) aqueous solution from Merck & Company under the tradename Merquat 100.

2. Other suitable polymers are the copolymers of dimethyldiallylammonium chloride and acrylamide having a molecular weight in the range of about 20,000 to 3,000,000. These polymers may be defined as poly (diallyldimethylammonium chloride-co-acrylamide) and include units of 1 above and acrylamide of the following structure in their structure:

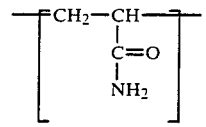

The amount of acrylamide type monomers incorporated in the copolymer may vary from 5% to 95% by weight of the total monomers. The copolymers can be made by subjecting the mixture of monomers to the same polymerization conditions as used in making the homopolymers described in 1 above. A preferred copolymer is available under the name Merquat 550 from Merck & Company. Merquat 550 contains 8% by weight of copolymer identified as PDDACA in water and such copolymer has a molecular weight of more than 500,000.

The polymers described in 1 an 2 above are described in U.S. Pat. Nos. 3,912,808, 3,986,825 and 4,027,008 incorporated by reference. The homopolymers and copolymers of aforesaid formulae can be prepared as described in U.S. Pat. Nos. 2,926,161, 3,288,770 or 3,412,019, the disclosure of these various patents being hereby incorporated by reference.

3. Quaternary derivatives of cellulose ethers sold by Union Carbide under the tradename, Polymer JR, in powdered form are described in U.S. Pat. No. 3,472,840 as having a molecular weight of from 100,000 to 3,000,000 and having the following structural formula:

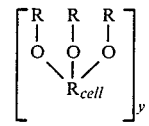

wherein $R_{cell}$ is the radical of an anhydroglucose unit, y is a number having a value of, say 50 to 20,000 and each R individually represents a substituent which is a group of the general formula:

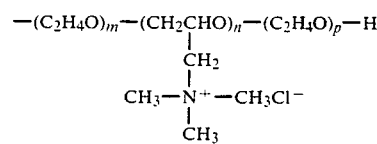

wherein m is an integer from 0 to 10, n is an integer from 1 to 3, and p is an integer from 0 to 10. The average values per anhydroglucose unit are n is from 0.35 to 0.45 and the sum of m+p is from 1 to 2. The viscosity of the "JR" Polymer ethers may vary from 50 to 35,000 centipoises at 25° C. in 2% by weight aqueous solutions when measured by ASTM method D-2364-65 (Model LVF Brookfield, 30 rpm, Spindle 2).

The specific group of anionic polymers used in present invention include:

1. Polysulfonic acid such as poly (2-acrylamido-2-methylpropane sulfonic acid) which is available under the name HSP 1180 Polymer from Henkel as a 15% aqueous solution by weight of the anionic polymer identified as PSA containing the following repeating structure:

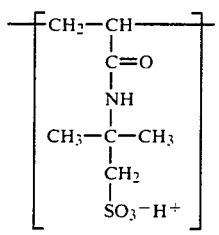

The molecular weight of such polymers varies from about 1,000,000 to about 5,000,000, preferably from about 2,500,000 to about 4,500,000. Usually, molecular weight is determined by the inherent viscosity of the polymer. The preparation of such polymers is described in, Canadian Pat. No. 864,433, which patent is incorporated by reference herein. As mentioned in said patent, the molecular weight of the polymer may be controlled by pH, the rate of addition of the monomer and the judicious use of a catalyst. Terminal groups on the polymer are not specified because they have little bearing on the properties of the polymer, but such groups are most often hydrogen.

2. Alginic acid in free acid form, which is water insoluble and available as a powder, has the following structural formula:

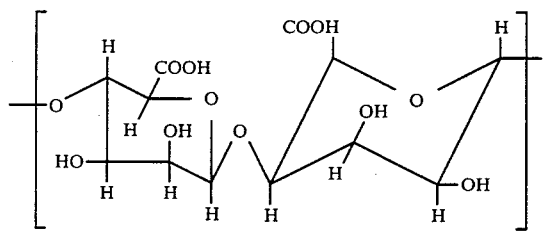

The interpolymer reaction of the foregoing polycationic and polyanionic materials produces reaction products ranging from insoluble precipitates to water soluble and water insoluble, but swellable, gels. The reaction product of poly (2-acrylamido-2-methylpropane sulfonic acid) (PSA) and Merquat 550 loses its fluidity and forms a clear gel when an aqueous mixture containing 7.5% by weight of PSA an 4% by weight of PDDACA is intensively mixed, while the individual solutions of the reactant polymers flow freely. When such gel is diluted to 2.85% by weight interpolymer reaction product, it still exhibits a high viscosity of more than 24,000 cps whereas corresponding reactant concentrations of the individual polymer solutions show viscosities of 400 cps and 200 cps, respectively. The minimum concentrationsrequired for the formation of a clear interpolymer gel reaction product of PSA and PDDACA contain 3.75% by weight of PSA and 2% by weight of PDDACA in the initial aqueous mixture. However, the interpolymer gel reaction product formed using said minimum concentrations can be diluted with water without loss of gelling properties. Such interpolymer gel reaction product is prepared by introducing 100 grams of a 7.5% weight concentration of PSA and 100 grams of a 4% weight concentration of PDDACA into a reaction vessel and intensivily mixing said mixture at 1000 rpm or more for from ten to thirty minutes. On the other hand, slow mixing results in white precipitates and a low viscosity reaction product. Also, further dilution of the two solutions before mixing results in white precipitates even when they are mixed intensively. This clearly indicates that it requires fast and intensive interactions of specified minimum concentrations of the two opposite charges to insure maximum amount of ion pair formation to give the gel structure. Whether the gel is water soluble or water insoluble depends on the formation of intimate or loose ion pairs which, in turn, depends on the charge density and structure of the polyelectrolytes.

The fast and intensive interactions of the two oppositely charged polymers necessary in the production of a gel as opposed to a precipitate require the essential reaction conditions of vigorous mixing of at least about 500 rpm, preferably about 1000 rpm, and selective anionic and cationic polymers in aqueous solutions containing minimal concentrations of anionic polymer and cationic polymer, depending on the specific polymer reactants.

The intermolecular reactions of anionic polymers and cationic polymers result in the formation of gels of various types ranging from water soluble to water insoluble depending upon the reaction conditions and the reactant plymer structures. More particularly, the reaction product of the PSA (Polymer I) and PDDACA (Polymer II) forms a clear water soluble gel when the minimum weight concentrations of 3.75% PSA and 2% PDDACA are present in the initial aqueous mixture which is subjected to intensive mixing. On the other hand, intensive mixing of Polymer I and poly(diallyldimethylammonium chloride)—Polymer III—forms an insoluble clear gel with extremely high viscoelasticity which can be easily made into film, with the minimum weight concentrations of Polymer I and Polymer III in the initial aqueous reaction mixture being 3.75% and 0.8% respectively. In addition, Polymer I and cationic cellulose ether polymer—Polymer IV—also form clear, water soluble gels upon being intensively mixed, with the minimum Polymer I and Polymer IV in the initial aqueous reaction mixture being 1.9% (about 2%) polymer I and 0.6% polymer IV by weight.

Minimum concentrations of the anionic and cationic polymer reactants are not critical where the anionic polymer is alginic acid —Polymer V—. Since alginic acid is water-soluble, its initial concentration in the aqueous reaction mixture is not significant. As the interpolymer reaction products of alginic acid and cationic PDDACA—Polymer II—or cationic quaternary ammonium cellulose ether—Polymer IV—are water soluble, the nature of the reaction is more complex. However, satisfactory clear interpolymer gels have been produced using intensive mixing when the calculated concentration of Polymer V in the initial reaction mixture is 1% by weight and concentration therein of Polymer II is 0.32% by weight or the concentration of Polymer IV is 1% by weight.

The ability of the aqueous interpolymer gel reaction product to retain its gelling properties upon further dilution with water taken in conjunction with the capacity to form a high viscosity at low concentrations in water make the inventive interpolymer gel reaction products an excellent candidate for sewage treatment since they could significantly improve drag reduction.

Gel formation does not depend on the ratio of the oppositely charged polymers present in the reaction mixture which need not be equimolecular, but can vary over a wide range, provided a minimal concentration of each reactant is present in the initial reaction medium (water). Slow stirring and concentrations of reactants below the minimum required amount specified herein causes precipitation and interferes with gel formation in water soluble gel. Similarly, dilution of each reactant below the minimum specified concentration prior to reaction, causes precipitation in lieu of gel formation. The presence of extraneous materials such as salts, acids, alkali, anionic surfactants, cationic surfactants and the like also interferes with the formation of a gel and causes precipitation of the complex. Accordingly, the aqueous reaction medium should be substantially free of extraneous materials. This clearly shows the specificity and criticality of the conditions of reaction.

The specificity of the polymer reactants is clearly shown by the reaction between 10 g PSA, a selective anionic polymer, and 5 g poly (methacrylamidopropyltriammonium chloride, a non-selective cationic polymer, which results in a milky white precipitate which does not break up after prolonged fast mixing. Similarly, the reaction between a polyacrylic acid polymer, a non-selective anionic polymer, and Merquat 550, a selective cationic polymer, in an aqueous medium produces a hazy gel which is indicative of the presence of precipitates in said gel.

The criticality of maintaining a minimum concentration of reactants is clearly shown by the reactions between HSP 1180 (15% by weight of PSA in water) and Merquat 550 (8% by weight of PDDACA in water) in varying concentrations. Intensive mixing of the mixture of 2 grams of Merquat 550 and 200 grams of a 3% PSA solution formed a precipitate which could not be dispersed by extensive stirring and which did not gel. When the quantity of Merquat 550 in the foregoing mixture was increased from 2 grams to 4 grams, a precipitate resulted which could not be dispersed. A further increase in the amount of Merquat 550 solution to 6 grams in said mixture also resulted in formation of a precipitate. However, when 4 grams of Merquat 550 was combined with 5.6 grams of HSP 1180 and subjected to intensive mixing, a thick gel formed which comprised 12.1% by weight of interpolymer gel reaction product and such gel swelled with the addition of 90 g of water to yield an aqueous gel containing 1.16% by weight of reaction product having a viscosity at 77° F. of 915 cps (Brookfield RVF viscometer, No. 3 Spindle, 20 rpm). In the latter experiment, the initial weight concentrations of anionic polymer and cationic polymer in the aqueous mixture were 8.8% and 3.3% respectively.

The resulting interpolymer gels are elastic and continuous in nature and capable of absorbing water in the formation of a very thick viscosity. Likewise, they retain their gel structure even upon dilution. They are stable and retain their gel structure when subjected to heat and/or cold. In addition, the viscosity of the gel does not permanently change as a result of heating and/or cooling. This unexpected feature is not possessed by the interpolymer gel disclosed in the cited *The Journal of Polymer Science,* (1976), wherein the viscosity thereof decreased permanently upon heating, and the final viscosity is determined by the temperature at which heating is stopped (page 770). The poly sulfonic acid-cationic interpolymer gels of present invention are superior to the alginic acid-cationic interpolymer gels in exhibiting a greater degree of elasticity, and a more continuous gel structure.

The foregoing discussion of this invention has concentrated on the minimum concentrations of the selective anionic and cationic polymers needed in the initial aqueous reaction medium in order to attain the desired aqueous interpolymer reaction product gel because of the criticality of this aspect of the invention in the formation of the water-soluble interpolymer reaction product of anionic PSA polymer and a quaternary ammonium cationic polymer selected from PDDACA and a quaternary ammonium cellulose ether polymer. While there is no discussion of the maximum concentration of either the polymeric reactants or the interpolymer reaction product in the aqueous medium, practically such maximum concentrations are limited by the viscosity of the resultant interpolymer reaction product which in turn must not exceed the viscosity at which the agitation is effective to achieve mixing of the reactants.

Similarly, no discussion of the maximum rate of agitation is deemed significant so long as the minimum effective speed of agitation of 500 rpm or more is achieved. Obviously, the speed of agitation above said minimum effective level varies with the type of agitator, e.g., propeller or turbine; the volume and viscosity of material being agitated; the size of the mixing vessel; and depending upon which of the foregoing factors apply, the speed of agitation to achieve effective mixing of the reactants may be increased to 1000 rpm or even 2000 rpm. Usually, such mixing takes place at about 75° F., although temperatures as high as 120° F. may be employed.

The following examples are merely illustrative of the invention, and are not to be construed as limiting thereof.

EXAMPLE 1

This example describes the reaction of anionic PSA polymer with cationic polymer PDDACA in the absence of intensive mixing.

The viscosity o various low concentrations of PSA polymer follow:

| HSP 1180 % by wt in water | Polymer (% by wt.) | Brookfield Viscosity (cps @ 77° F.) Spindle #1 @ 20 rpm |
| --- | --- | --- |
| 1 | .15 | 80 |
| 2 | .30 | 150 |
| 3 | .45 | 181 |
| 4 | .6 | 184.5 |
| 5 | .75 | 237.5 |
| 6 | .9 | 277.5 |

The viscosity of various low concentrations of PDDACA polymer in water follows:

| Merquat 550 % by wt. in water | PDDACA (% by wt.) | Brookfield Viscosity (cps @ 77° F.) Spindle #1 @ 20 rpm |
| --- | --- | --- |
| 0.5 | .04 | 12.5 |
| 1 | .08 | 12.5 |
| 2 | .16 | 22.5 |
| 3 | .24 | 20.0 |

When the following proportions of HSP 1180 (15% solution of PSA by weight) and Merquat 550 (8% of PDDACA by weight) are added together and mixed with slow agitation and the resultant product is diluted to 200 g. with water, aqueous interpolymer reaction products having the following properties are obtained:

| Sample | HSP 1180 g. | Merquat 550 g. | Aqueous Interpolymer Reaction Product | | |
|---|---|---|---|---|---|
| | | | Interpolymer % by wt. | Viscosity(a) cps | Appearance |
| G-1 | 2.8 | 2 | .29 | 59 | Precipitate |
| G-2 | 2.8 | 4 | .37 | 46 | Precipitate |
| G-3 | 5.6 | 2 | .50 | 100 | Precipitate |
| G-4 | 5.6 | 4 | .58 | 95.5 | Almost Clear |

(a)Brookfield RVF viscometer. #1 spindle rotating at 20 rpm.

The foregoing tabulation clearly shows that interpolymer reaction products which form clear gels in water are not obtained in the absence of intensive agitation. More specifically, the viscosity of low concentrations of interpolymer reaction product is less than the viscosity of similar concentrations of the anionic PSA polymer in water. Further, the resultant interpolymer reaction product is not completely soluble in water.

EXAMPLE 2

Using the same reactants as in Example 1, namely, HSP 1180 (15% solution of PSA by weight) and Merquat 550 (8% solution of PDDACA by weight), the following interpolymer reaction products are prepared by introducing the two aqueous polymer mixtures into a mixing vessel and intensively mixing said reactants by agitating at a speed of about 1000 rpm for about ten minutes to form the described interpolymer gel compositions

| Sample | HSP 1180 g | Merquat 550 g | Concentration of Interpolymer Reaction Product Weight Percent |
|---|---|---|---|
| S-1 | 8.4 | 0 | 0 |
| S-2 | 8.4 | 2 | 13.7 |
| S-3 | 8.4 | 4 | 12.7 |
| S-4 | 8.4 | 6 | 12.1 |
| S-5 | 8.4 | 8 | 11.6 |
| S-6 | 12.6 | 0 | 0 |
| S-7 | 12.6 | 3 | 13.7 |
| S-8 | 12.6 | 6 | 12.7 |
| S-9 | 12.6 | 9 | 12.1 |
| S-10 | 12.6 | 12 | 11.6 |

Each of the above-identified samples was diluted to 100 g. by weight with deonized water and the viscosity of the resultant interpolymer solution was determined using a Brookfield RVF Viscometer. The results are tabulated below:

| Sample | Interpolymer Conc. by weight | Brookfield Viscosity (cps @ 77° F.) | |
|---|---|---|---|
| | | Spindle #3 @ RPM | Spindle #3 @ 2 RPM |
| S-1 | 0 | 250 | — |
| S-2 | 1.42 | 620 | — |
| S-3 | 1.58 | 1550 | — |
| S-4 | 1.74 | 2630 | — |
| S-5 | 1.92 | 4050 | — |
| S-6 | 0 | 400 | 550 |
| S-7 | 2.12 | 1755 | 3100 |
| S-8 | 2.36 | 4020 | 11200 |
| S-9 | 2.60 | 6650 | 18650 |
| S-10 | 2.84 | 9500 | 24850 |

The foregoing results clearly show that the interpolymer reaction product of PSA and PDDACA acts as a gellant at interpolymer concentrations in the range of 1.42% to 2.84% by weight. Further, the clear gels are thixotropic because the viscosity increases as the shear rate is decreased.

the thixotropic nature of the S-10 sample is illustrated further in the following tabulation which describes the viscosity results obtained using other spindles and shear rates:

| Shear Sensitivity of S-10 Gel | | |
|---|---|---|
| | Brookfield Viscosity (cps @ 77° F.) | |
| RPM | Spindle #5 | Spindle #6 |
| 2 | 28,600 | 29,500 |
| 4 | 21,600 | 22,250 |
| 10 | 14,680 | 14,800 |
| 20 | 10,920 | 10,500 |

EXAMPLE 3

126 g of HSP 1180 (15% solution) of Example 1 and 120 g of Merquat 550 (8% solution) of Example 1 are rapidly mixed as described in Example 2 to produce a gel containing 11.6% by weight of interpolymer reaction product. (The weight concentrations of anionic PSA polymer and cationic PDDACA polymer in the initial reaction mixture are 7.7% and 3.9% respectively.) The Brookfield viscosity of the gel is greater than 500,000 cps (Brookfield Model RVF Viscometer, #7 spindle, 2 rpm.) This is a preferred gel.

EXAMPLE 4

125 g of HSP 1180 (15% solution), the anionic polymer of Example 1, are rapidly mixed with 24 g of Merquat 100 (40% aqueous solution). A clear, water insoluble gel containing 19% by weight of interpolymer reaction product is formed which is very viscoeleastic and easily forms a film. It sticks to the beaker, but can be removed after being immersed in water for a period of time.

EXAMPLE 5

50 g of HSP 1180 (15% solution) of Example 1 and 100 g of a 5% solution of Polymer JR-400 (quaternized cellulose ether polymer) are introduced into a mixing vessel and mixed at a speed of about 1000 rpm for about twenty minutes. The initial mixture contains 5% by weight of PSA and 3.33% by weight of Polymer JR-400 and loses its fluidity upon agitation. A clear water soluble gel containing 8.33% by weight of interpolymer reaction product solution is formed which appears to be less stringy than the gels of Example 2 (PDDACA and PSA polymers).

EXAMPLE 6

1 g of Kelacid (alginic acid) is added to 50 g of Merquat 550 (8% solution) while stirring rapidly at about 1000 rpm. The insoluble Kelacid gradually dissolves and a clear water soluble gel is formed which contains 9.8% by weight of the interpolymer reaction product. The calculated weight percentages of cationic PDDACA polymer and anionic alginic acid polymers in the mixture are 7.8% and 2% respectively.

EXAMPLE 7

50 g of Merquat 550 (8% A.I.) is mixed with 50 g. of deionized water and to this mixture is added a mixture of 50 g of HSP 1180 (15%) dilutedwith 50 g solution of deionized water in a mixing vessel. After agitating at about 1000 rpm for about 20 minutes, a thick gel is formed which shows almost no fluidity and is transparent. Such gel contains 11.5% by weight of the interpolymer reaction product and the weight concentrations of anionic polymer and cationic polymer in the initial mixture are 7.5% and 4% respectively.

However, when 5 g of Merquat 550 (8% A.I.) diluted with 95 g of water is mixed with 5 g of HSP 1180 (15% A.I.) diluted with 95 g of water in the manner described in Example 2, a white, sticky precipitate is obtained which did not go into solution upon agitation. Since the desired interpolymer gel is not obtained, this example clearly shows the criticality of using certain minimum concentratins of reactants in the initial mixture of effect gel formation. (The proportions of anionic polymer and cationic polymer in the initial mixture are 0.75% and 0.4% on a weight basis.)

EXAMPLE 8

An interpolymer reaction product of Polymer JR-400 and Kelacid (alginic acid) is prepared according to the following formula:

| Ingredients | g |
|---|---|
| Polymer JR-400 (5% solution) | 20 |
| Deionized Water | 79 |
| Kelacid | 1 |

The Kelacid is added to the solution of Polymer JR-400 in deionized water with intensive agitation using the process described in Example 6. The insoluble Kelacid becomes soluble after a few minutes of mixing and forms a water soluble gel containing 2% by weight of the interpolymer reaction product. In this instance, a 1% weight concentration of cationic polymer in water reacted with pure anionic alginic acid polymer. (The calculated concentration of cationic polymer in the final mixture is 1% by weight.)

EXAMPLE 9

The reaction between 2.6 g of HSP 1180 (15% solution by weight) and 20 g of Polymer JR-400 (5% solution) by weight in the manner described in Example 2, results in a clear gel which contains 6.% by weight of the interpolymer reaction product. While the described process describes the mixing of 15% weight concentration of anionic PSA polymer with a 5% concentration of cationic Polymer JR-400, the weight concentrations of anionic polymer and cationic polymer in the initial mixture are 4.4% and 1.7% respectively. Yet dilution of the 6.1% polymer concentration with 67.4 g of water yields an interpolymer solution containing 1.39% by weight of interpolymer reaction product having a viscosity of 59,000 cps at 77° F. (Brookfield RVF viscometer, #4 spindle rotating at 2 rpm).

EXAMPLE 10

100 g of Polymer JR solution (4.25% by weight of polymer) is added to 100 g of PSA solution (11.25% by weight of PSA) and is subjected to intensive mixing by agitating at about 1000rpm for ten minutes to yield a clear gel containing 7.75% by weight of interpolymer reaction product.

EXAMPLE 11

Example 10 is repeated except that the Polymer JR solution contains 1.75% by weight of polymer and the PSA solution contains 5.25% by weight of polymer.

The resultant clear gel contains 3.5% by weight of interpolymer reaction product.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

What is claimed is:

1. A clear gel in water which comprises water containing the reaction product formed by the rapid and intensive agitation of a cationic polymer bearing a positive charfe selected from the group consisting of poly (diallyldimethylammonium chloride), poly(diallyldimethylammonium chloride-co-acrylamide), and a quaternary ammonium cellulose ether polymer and an anionic polymer bearing a negative charge selected from the group consisting of polysulfonic acid and alginic acid, said gel having a viscosity sufficient to yield a viscosity upon dilution with water which exceeds the viscosity of a corresponding aqueous concentration of the individual polymers.

2. The interpolymer gel of claim 1 which is a clear gel free of precipitates.

3. A clear, water soluble, interpolymer gel in accordance with claim 1 which is the interpolymer reaction product of anionic poly (2-acrylamido-2-methylpropane sulfonic acid) polymer with cationic poly (diallyldimethylammonium chloride-co-acrylamide) polymer in an aqueous medium, the initial aqueous mixture containing at least 3.75% by weight of said anionic polymer and at least 2% by weight of said cationic polymer.

4. A clear, water insoluble, interpolymer gel according to claim 1 which is the reaction product of anionic poly (2-acrylamido-2-methylpropane sulfonic acid) polymer with cationic poly (diallyldimethylammonium chloride) polymer in an aqueous medium, the initial aqueous mixture containing at least 3.75% by weight of said anionic polymer and at least 2% by weight of said cationic polymer.

5. A clear, water soluble, interpolymer gel according to claim 1 which is the reaction product of anionic poly (2-acrylamido-2-methylpropane sulfonic acid) polymer with a cationic quaternary ammonium cellulose ether polymer in an aqueous medium, the initial aqueous mixture containing at least 1.9% by weight of said anionic polymer and at least 0.6% by weight of said cationic polymer.

6. A clear, water soluble, interpolymer gel according to claim 1 which is the reaction product of effective amounts of anionic alginic acid with cationic poly (diallyldimethylammonium chloride-co-acrylamide) polymer in an aqueous medium.

7. A clear, water soluble interpolymer gel according to claim 6 wherein the initial aqueous mixture contains at least 1% by weight of said alginic acid and at least 0.32% by weight of said cationic polymer.

8. A clear, water soluble, interpolymer gel according to claim 1 which is the reaction product of effective amouts of alginic acid with a quaternary ammonium cellulose ether polymer in an aqueous medium.

9. A clear, water soluble, interpolymer gel according to claim 8 wherein the initial aqueous mixture contains at least 1% by weight of said alginic acid and at least 1% by weight of said cationic polymer.

10. The method of forming the interpolymer gel in accordance with claim 1, which comprises the rapid mixing at an agitation of at least 500 rpm of effective concentrations of selective anionic and selective cationic polymers in an aqueous medium substantially free of extraneous materials which interfere with the formation of gel structure, said anionic polymer being selected from the group consisting of polysulfonic acid and alginic acid and said cationic polymer is a quaternized polymer selected from the group consisting of poly (diallyldimethylammonium chloride) polymer, poly (diallyldimethylammonium chloride-co-acrylamide) polymer and a quaternary ammonium cellulose ether.

11. The method in accordance with claim 10 wherein said speed of agitation is at least about 1000 rpm.

* * * * *